US009814697B2

(12) United States Patent
Patel et al.

(10) Patent No.: US 9,814,697 B2
(45) Date of Patent: Nov. 14, 2017

(54) COMPOSITION FOR NONALCOHOLIC FATTY LIVER DISEASE (NAFLD)

(71) Applicant: Cadila Healthcare Limited, Ahmedabad, Gujarat (IN)

(72) Inventors: Pankaj Patel, Gujarat (IN); Rajendrakumar Hariprasad Jani, Gujarat (IN)

(73) Assignee: CADILA HEALTHCARE LIMITED, Ahmedabad, Gujarat (IN)

(*) Notice: Subject to any disclaimer, the term of this patent is extended or adjusted under 35 U.S.C. 154(b) by 0 days.

(21) Appl. No.: 15/343,859

(22) Filed: Nov. 4, 2016

(65) Prior Publication Data
US 2017/0087127 A1 Mar. 30, 2017

Related U.S. Application Data

(62) Division of application No. 14/782,609, filed as application No. PCT/IN2013/000391 on Jun. 25, 2013, now abandoned.

(30) Foreign Application Priority Data

Apr. 22, 2013 (IN) .......................... 1468/MUM/2013

(51) Int. Cl.
A61K 31/40 (2006.01)
(52) U.S. Cl.
CPC ........... *A61K 31/40* (2013.01); *Y10S 514/893* (2013.01)
(58) Field of Classification Search
None
See application file for complete search history.

(56) References Cited

U.S. PATENT DOCUMENTS

| 4,231,938 | A | 11/1980 | Monaghan et al. |
| 4,346,227 | A | 8/1982 | Terahara et al. |
| 4,444,784 | A | 4/1984 | Hoffman et al. |
| 5,273,995 | A | 12/1993 | Roth |
| 5,354,772 | A | 10/1994 | Kathawala |
| 6,166,063 | A | 12/2000 | Villhauer |
| 6,395,767 | B2 | 5/2002 | Robl et al. |
| 6,699,871 | B2 | 3/2004 | Edmondson et al. |
| 6,987,123 | B2 | 1/2006 | Lohray et al. |
| 7,041,837 | B2 | 5/2006 | Lohray et al. |
| 7,323,491 | B2 | 1/2008 | Lohray et al. |
| 7,407,955 | B2 | 8/2008 | Himmelsbach et al. |
| 8,110,598 | B2 | 2/2012 | Lohray et al. |
| 8,212,057 | B2 | 7/2012 | Lohray et al. |
| 8,558,009 | B2 | 10/2013 | Lohray et al. |
| 8,772,342 | B2 | 7/2014 | Darteil et al. |
| 2003/0199498 | A1 | 10/2003 | Lohray et al. |
| 2003/0236254 | A1 | 12/2003 | Lohray et al. |
| 2007/0238776 | A1 | 10/2007 | Lohray et al. |
| 2011/0275669 | A1 | 11/2011 | Lohray et al. |
| 2012/0121729 | A1 | 5/2012 | Paterson et al. |
| 2013/0338209 | A1 | 12/2013 | Gambhire et al. |
| 2016/0068484 | A1 | 3/2016 | Jain et al. |
| 2016/0107989 | A1 | 4/2016 | Dwivedi et al. |
| 2016/0136131 | A1 | 5/2016 | Patel et al. |
| 2016/0166539 | A1 | 6/2016 | Patel et al. |
| 2016/0194280 | A1 | 7/2016 | Dwivedi et al. |
| 2016/0207884 | A1 | 7/2016 | Dwivedi et al. |

FOREIGN PATENT DOCUMENTS

| EP | 1586571 A1 | 10/2005 |
| IN | 1910/MUM/2013 | 12/2014 |
| WO | WO-91/19702 A1 | 12/1991 |
| WO | WO-94/01420 A1 | 1/1994 |
| WO | WO-94/13650 A1 | 6/1994 |
| WO | WO-95/03038 A1 | 2/1995 |
| WO | WO-95/17394 A1 | 6/1995 |
| WO | WO-96/04260 A1 | 2/1996 |
| WO | WO-96/04261 A1 | 2/1996 |
| WO | WO-96/33998 A1 | 10/1996 |
| WO | WO-97/25042 A1 | 7/1997 |
| WO | WO-97/36579 A1 | 10/1997 |
| WO | WO-99/08501 A2 | 2/1999 |
| WO | WO-99/16758 A1 | 4/1999 |
| WO | WO-99/19313 A1 | 4/1999 |
| WO | WO-99/20614 A1 | 4/1999 |
| WO | WO-00/23417 A1 | 4/2000 |

(Continued)

OTHER PUBLICATIONS

Lemonie et al.,Steatohepatitis(fatty liver) Is Associated With Increased Hepatic Expression of SREBP-1 in HIV-Infected Patients With Antiretroviral Therapy-Linked Lipodystrophy, 55th Annual Meeting of the American association for the Study of Liver Diseases Oct. 29-Nov. 2, 2004,printed from http://www.natap.org/2004/AASLD/aasld_10.htm, 8 pages.*
Angulo, GI epidemiology: nonalcoholic fatty liver disease, Aliment Pharmacol Ther. Apr. 15, 2007;25(8):883-9.*
Bugianesi et al., Insulin resistance: a metabolic pathway to chronic liver disease, Hepatology. Nov. 2005;42(5):987-1000.*
Herrine, Nonalcoholic Steatohepatitis (NASH), Merck Manual, May 2016, printed from http://www.merckmanuals.com/professional/hepatic-and-biliary-disorders/approach-to-the-patient-with-liver-disease/nonalcoholic-steatohepatitis-nash, 3 pages.*
Boettcher et al., Meta-analysis: pioglitazone improves liver histology and fibrosis in patients with non-alcoholic steatohepatitis, Aliment Pharmacol Ther. Jan. 2012;35(1):66-75. doi: 10.1111/j.1365-2036.2011.04912.x. Epub Nov. 4, 2011, printed from https://www.ncbi.nlm.nih.gov/pubmed/22050199.*

(Continued)

*Primary Examiner* — Gigi Huang
(74) *Attorney, Agent, or Firm* — Goodwin Procter LLP

(57) ABSTRACT

The present invention provides a compound of Formula (I) or pharmaceutical acceptable thereof, wherein 'R' is herein described. In addition, the invention relates to composition comprising effective therapeutic amount of compound of formula (I) and methods of using the compounds for treating or prevention disorder such as nonalcoholic fatty liver disease (NAFLD) including fatty liver (steatosis), nonalcoholic steatohepatitis (NASH), and cirrhosis (advanced scarring of the liver).

6 Claims, 4 Drawing Sheets

(56) References Cited

FOREIGN PATENT DOCUMENTS

| | | |
|---|---|---|
| WO | WO-00/23445 A1 | 4/2000 |
| WO | WO-00/23451 A1 | 4/2000 |
| WO | WO-01/53257 A2 | 7/2001 |
| WO | WO-02/24625 A2 | 3/2002 |
| WO | WO-03/009841 A1 | 2/2003 |
| WO | WO-2005/031335 A1 | 4/2005 |
| WO | WO-2012/104869 A1 | 8/2012 |
| WO | WO-2014/174524 A1 | 10/2014 |
| WO | WO-2014/195967 A2 | 12/2014 |
| WO | WO-2015/001573 A1 | 1/2015 |
| WO | WO-2015/011730 A1 | 1/2015 |
| WO | WO-2015/029066 A1 | 3/2015 |
| WO | WO-2015/033357 A2 | 3/2015 |

OTHER PUBLICATIONS

Boulet in "Influence of Comorbid Conditions on Asthma" in *European Respiratory Journal* (2009) vol. 33, pp. 897-906.

Chatila et al. in "Comorbidities in Chronic Obstructive Pulmonary Disease" in *Proc. Am. Thorac. Soc.* (2008) vol. 5, pp. 549-555.

Jackson in "No Benefit from Ezetimibe in NASH" in Medpage Today (Jun. 2015).

Prescribing Information for Zetia® (ezetimibe; year 2012).

Rakoski et al. in "Meta-analysis: Insulin Sensitizers for the Treatment of Non-alcoholic Steatohepatitis" in *Aliment. Pharmacol. Ther.* (2010) vol. 32, pp. 1211-1221.

International Search Report and Written Opinion dated Feb. 2, 2015 for International Patent Application No. PCT/IN2014/000367 (14 pages).

Jani, R. H. et al. "Pharmacokinetics, Safety, and Tolerability of Saroglitazar (ZYH1), a Predominantly PPARα Agonist with Moderate PPARγ Agonist Activity in Healthy Human Subjects" *Clin. Drug Investig.* (2013) vol. 33, pp. 809-816.

Brenna, E. et al. "Enzyme-mediated synthesis of EEHP and EMHP, useful pharmaceutical intermediates of PPAR agonists" *Tetrahedron: Asymmetry* (2009) vol. 20, pp. 2594-2599.

International Search Report and Written Opinion dated Mar. 23, 2015 for Application No. PCT/IN2014/000584 (14 pages).

International Search Report and Written Opinion dated Dec. 19, 2014 for Application No. PCT/IN2014/000551 (11 pages).

Demuth, H.-U. et al. "Type 2 diabetes—Therapy with dipeptidyl peptidase IV inhibitors," *Biochim. Biophys. Acta*, 1751 (2005) pp. 33-44.

Augustyns, K. et al. "Inhibitors of proline-specific dipeptidyl peptidases: DPP IV inhibitors as a novel approach for the treatment of Type 2 diabetes," *Expert Opin. Ther. Patents*, (2005) vol. 15, No. 10, pp. 1387-1407.

Pai, V. et al. "A Multicenter, Prospective, Randomized, Double-blind Study to Evaluate the Safety and Efficacy of Saroglitazar 2 and 4 mg Compared to Pioglitazone 45 mg in Diabetic Dyslipidemia (PRESS V)." *J. Diabetes Sci. Technol.* (2014) vol. 8, No. 1, pp. 132-141.

Jani, R. H. et al. "A Multicenter, Prospective, Randomized, Double-Blind Study to Evaluate the Safety and Efficacy of Saroglitazar 2 and 4 mg Compared with Placebo in Type 2 Diabetes Mellitus Patients Having Hypertriglyceridemia Not Controlled with Atorvastatin Therapy (Press VI)," Diabetes Technology & Therapeutics, (2014) vol. 16, No. 2, pp. 63-71.

International Search Report and Written Opinion dated Dec. 23, 2014 for International Patent Application No. PCT/IN2014/000445 (10 pages).

International Preliminary Report on Patentability dated Oct. 6, 2015 for International Patent Application No. PCT/IN2014/000445 (7 pages).

Ansel et al. "Pharmaceutical Dosage Forms and Drug Delivery Systems, Seventh Edition" 1999, pp. 88-92.

Cairns, D. (editor) "Essentials of Pharmaceutical Chemistry, Fourth Edition" 2012, p. 14.

Bharate, S. et al. "Interactions and incompatibilities of pharmaceutical excipients with active pharmaceutical ingredients: a comprehensive review." *J. Excipient and Food Chem.* (2010) vol. 1, No. 3, pp. 3-26.

International Search Report and Written Opinion dated Nov. 20, 2014 for International Application No. PCT/IN2014/000489 (10 pages).

International Preliminary Report on Patentability dated Oct. 9, 2015 for International Application No. PCT/IN2014/000489 (7 pages).

Response to Written Opinion filed on May 21, 2015 for International Application No. PCT/IN2014/000489 (6 pages).

"Sodium Stearyl Fumarate", obtained on Jun. 23, 2015. Retrieved from the Internet: <URL: https://www.medicinescomplete.com/me/excipients/current/ . . . >, 4 pages.

Lieberman, et al. "Pharmaceutical Dosage Forms: Tablets, vol. 1, 2nd Edition" (1989) Marcel Dekker Inc., pp. 111-114.

Gennaro et al. "Remington's Pharmaceutical Sciences, 19th Edition" (1995) Mack Publishing, pp. 1380-1383.

Anonymous International Nonproprietary Names for Pharmaceutical Substances (INN); Jan. 1, 2012; Retrieved from the internet: URL: http://www.who.int/medicines/publications/druginformation/issues/PL_108.pdf; Retrieved on Oct. 15, 2013; pp. 401-471.

International Search Report and Written Opinion dated Nov. 20, 2013 for International Application No. PCT/IN2013/000391 (13 pages).

International Preliminary Report on Patentability dated Jul. 9, 2015 for International Application No. PCT/IN2013/000391 (9 pages).

IND Committee: "Minutes of IND Committee Meeting Held on Jul. 19, 2012" Retrieved on Oct. 15, 2013 from the Internet from URL: http://www.docstoc.com/docs/145152750/IND-Minutes-draft-19-07-12 (2 pages).

Anonymous "IND Minutes draft Jul. 19, 2012" Retrieved on Oct. 15, 2013 from the Internet from URL: http://www.docstoc.com/docs/145152750/IND-Minutes-draft-19-07-12 (1 page).

Anonymous "Lipaglyn™ Discovery, Development & Preclinical Studies" Retrieved on Oct. 15, 2013 from the Internet from URL: http://webcache.googleusercontent.com/search?q=cache:RGrhmY0HM3sJ:lipaglyn.com/downloads/Lipaglyn_Preclinical_Studies.ppsx (25 pages).

Jani, R. H. et al. "A Prospective Randomized, Double Blind, Placebo Controlled Study to Evaluate the Safety, Tolerability and Pharmacokinetics of ZYH1 Following Once a Day (OD) Oral Administrations up to 10 Days in Healthy Volunteers," *Diabetes* (2009) vol. 58, No. Suppl. 1, p. A569.

Ramirez, T. et al. "Structural Correlates of PPAR Agonist Rescue of Experimental Chronic Alcohol-Induced Steatohepatitis," *J. Clin. Exper. Pathology* (2012) vol. 2, No. 4, pp. 1-9.

Seo, Y. S. et al. "PPAR agonists treatment is effective in a nonalcoholic fatty liver disease animal model by modulating fatty-acid metabolic enzymes" *J. Gatroenterology Hepatology* (2008) vol. 23, No. 1, pp. 102-109.

Barb et al. (2016) "Pharmacological management of nonalcoholic fatty liver disease" Metabolism Clinical and Experimental 65:1183-1195.

Berger et al. (2005) "PPARs: Therapeutic targets for metabolic disease" TRENDS in Pharmacological Sciences 26(5): 244-251.

Chou et al. (2013) "Metrelepin: First Global Approval" Drugs 73:989-997.

Deeg et al. (2007) "Pioglitazone and Rosiglitazone Have Different Effects on Serum Lipoprotein Particle Concentrations and Sizes in Patients With Type 2 Diabetes and Dyslipidemia" Diabetes Care 30(10):2458-2464.

FDA News Release—FDA Approves Egrifta to treat Lipodystrophy in HIV Patients; downloaded from www.fda.gov/NewsEvents/Newsroom/PressAnnouncements/ucm233516.htm on Sep. 7, 2016 (2 pages).

Giri et al. "Efficacy of Saroglitazar, a Novel PPAR Agonist in a Mouse Model of Non-Alcoholic Steatohepatitis" Poster No. 2011, Keystone Symposia Conference, Mar. 22-27, 2015 at Whistler, British Colombia, Canada.

Jain et al. "Saroglitazar Shows Therapeutic Benefits in Mouse Model of Non-alcoholic Fatty Liver Disease (NAFLD) and Non-

(56) References Cited

OTHER PUBLICATIONS alcoholic Steatohepatitis (NASH)" Poster No. 1957-P, 75th Scientific Session—ADA, Jun. 5-9, 2015, Boston, MA, USA.
Package Insert for ACTOS (pioglitazone) tablets for oral use (2013).
Package Insert for AVANDIA (rosiglitazone maleate) Tablets (2008).
Palomer et al. (2016) "PPARβ/δ and lipid metabolism in the heart" Biochemica et Biophysica Acta 1861:1569-1578.
Yessoufou et al. (2010) "Multifaceted roles of peroxisome proliferator-activated receptors (PPARs) at the cellular and whole organism levels" Swiss Medical Weekly 140:w13071.
International Search Report dated May 9, 2012 for International Application No. PCT/IN2012/000069 (3 pages).
van Wijk, J. P. H. et al. "Comparison of Rosiglitazone and Metformin for Treating HIV Lipodystrophy: A Randomized Trial," *Ann. Internal Med.* (2005) vol. 143, No. 5, pp. 337-346.
Hadigan, C. et al. "Metabolic Effects of Rosiglitazone in HIV Lipodystrophy: A Randomized, Controlled Trial," *Ann. Internal Med.* (2004) vol. 140, No. 10, pp. 788-794. (Abstract Only).
Macallan, D. C. et al. "Treatment of Altered Body Composition in HIV Associated Lipodystrophy: Comparison of Rosiglitazone, Pravastatin, and Recombinant Human Growth Hormone," *HIV Clinical Trials*, (2008) vol. 9, Issue 4, pp. 254-268. (Abstract Only).
Tungsiripat, M. et al. "Rosiglitazone improves lipoatrophy in patients receiving thymidine-sparing regimens," *AIDS*, (2010) vol. 24, pp. 1291-1298.
Fan, W. and Evans, R. "PPARs and ERRs: molecular mediators of mitochondrial metabolism" *Curr. Opin. Cell Bio.* (2015) vol. 33, pp. 49-54.
LaBrecque, D. et al. "World Gastroenterology Organisation, Global Guidelines: Nonalcoholic Fatty Liver disease and Nonalcoholic Steatohepatitis (long version)" World Gastroenterology Organisation (2012) 29 pages.
International Preliminary Report on Patentability dated Aug. 15, 2013 for International Application No. PCT/IN2012/000069 (5 pages).
International Preliminary Report on Patentability dated Dec. 1, 2015 for International Patent Application No. PCT/IN2014/000367 (9 pages).
International Preliminary Report on Patentability dated Mar. 1, 2016 for Application No. PCT/IN2014/000551 (7 pages).
International Preliminary Report on Patentability dated Mar. 8, 2016 for International Patent Application No. PCT/IN2014/000584 (10 pages).
Written Opinion of the International Searching Authority dated May 9, 2012 for International Application No. PCT/IN2012/000069 (4 pages).

\* cited by examiner

COMPOSITION FOR NONALCOHOLIC FATTY LIVER DISEASE (NAFLD)

CROSS-REFERENCE TO RELATED APPLICATIONS

This application is a divisional of U.S. patent application Ser. No. 14/782,609, filed Oct. 6, 2015, which is the national stage of International (PCT) Patent Application Serial No. PCT/IN2013/000391, filed Jun. 25, 2013, which claims the benefit of and priority to Indian Patent Application serial number 1468/MUM/2013, filed Apr. 22, 2013; the contents of each of which are hereby incorporated by reference.

FIELD OF THE INVENTION

The present invention relates to pharmaceutical compositions containing the formula (I)

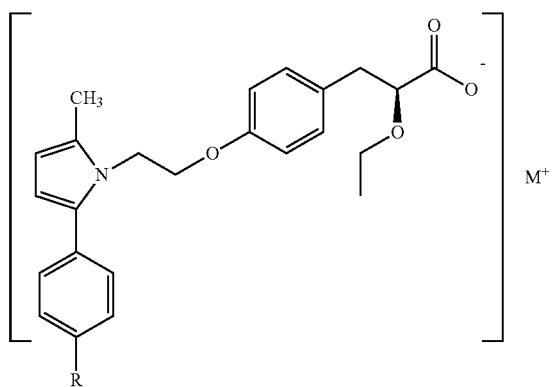

for the reduction and removal of lipid accumulated in the liver cells (hepatocytes) which is associated with nonalcoholic fatty liver disease (NAFLD). The present invention further provides the composition of formula (I) useful in the prevention and treatment of nonalcoholic fatty liver disease (NAFLD)

BACKGROUND OF THE INVENTION

Nonalcoholic fatty liver disease (NAFLD) refers to a wide spectrum of liver disease ranging from simple fatty liver (steatosis), to nonalcoholic steatohepatitis (NASH), to cirrhosis (irreversible, advanced scarring of the liver). All of the stages of NAFLD have in common the accumulation of fat (fatty infiltration) in the liver cells (hepatocytes). In NASH, the fat accumulation is associated with varying degrees of inflammation, fibrosis and scarring of the liver.

NASH and NAFLD are frequently reported in both men and women, although it most often appears in women and is especially prevalent in the obese. Although the disease has been observed to be accompanied by several other pathological conditions, including diabetes mellitus, hyperlipidemia, hyperglycemia, all part of the "metabolic syndrome," the cause and progression of the disease, as well as the causal or temporal relation to these conditions, is not well understood.

However, in patients suffering from NAFLD and NASH in particular, certain characteristics of liver tissue and abnormalities of function are typical. Specifically, fatty deposits, tissue degeneration, inflammation, cell degeneration, fibrosis, cirrhosis, elevation of free fatty acids and other such abnormalities have come to be associated with nonalcoholic steatohepatitis and are frequently seen in patients suffering from different forms of NAFLD.

The physiological condition that most commonly accompanies NASH is obesity, with approximately 70% and above of NASH sufferers also displaying clinically diagnosed obesity. NASH is particularly prevalent in obese patients who have undergone jejunal bypass to treat the obesity. In NASH patients, the extent of obesity tends to be generally correlated with the amount of steatosis and to be unrelated to non-insulin-dependent diabetes mellitus. However, non-insulin-dependent diabetes mellitus increases the prevalence of steatohepatitis especially in patients requiring insulin. Unless a massive amount of the excess body weight is eliminated, weight loss in patients before death does not appear to alleviate the steatosis and, somewhat paradoxically, obese patients who lost weight before death can have a higher incidence of steatohepatitis.

Even in NASH patients who do not consume any alcohol at all, liver biopsy specimens tend to mimic those seen in patients suffering from alcoholic hepatitis. However, a comparison of the two conditions reveals a higher incidence of vacuolation (indicative of diabetes) and steatosis in NASH as compared to alcoholic hepatitis. Patients suffering from alcoholic hepatitis also have a higher incidence of periportal and pericellular fibrosis and proliferation of the bile ducts. Overall, the symptoms and histological damage observed in alcoholic hepatitis patients are more severe than in NASH.

Currently, there is no established therapy for patients suffering from NASH. Weight loss is a common prescription, simply because obesity is frequently detected in patients suffering from NASH. The effect of a reduction in weight loss on NASH cannot be determined with certainty, however, because obese patients seldom maintain significant weight reduction. Thus, there is a need to find a treatment for NAFLD and particularly NASH.

Objects of the Invention

In one embodiment, the present invention discloses a pharmaceutical composition containing the compound of the Formula (I)

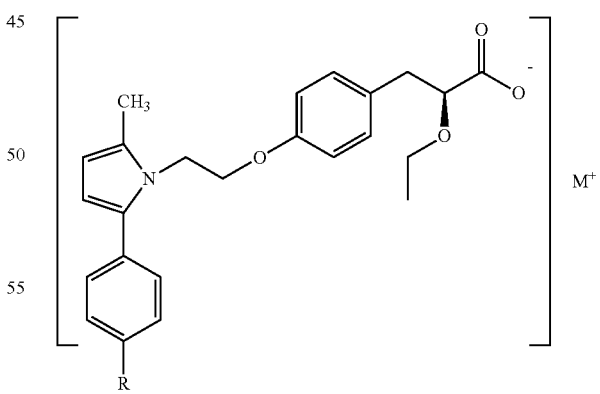

for reduction and removal of lipid accumulated in the liver cells (hepatocytes), required for treating and preventing certain diseases and conditions related to nonalcoholic fatty liver disease (NAFLD) including fatty liver (steatosis), nonalcoholic steatohepatitis (NASH), and cirrhosis (advanced scarring of the liver) in patient in need of such treatment.

In another embodiment the present invention provides a method and a formulation comprising an effective amount of compound of Formula (I) for treating nonalcoholic fatty liver disease (NAFLD) including fatty liver (steatosis), nonalcoholic steatohepatitis (NASH), and cirrhosis (advanced scarring of the liver).

The method comprises administering to a subject an effective amount of a compound of formula (I) as a pharmaceutical formulation, as disclosed hereinafter including pharmaceutically acceptable salts of the compound of formula (I).

In yet another embodiments the invention further provides a pharmaceutical composition containing effective amount of compound of formula (I) suitable for treatment of nonalcoholic fatty liver disease (NAFLD) including fatty liver (steatosis), nonalcoholic steatohepatitis (NASH), and cirrhosis (advanced scarring of the liver).

In another embodiment the present invention provides a method of treating alcoholic steatohepatitis in a subject, comprising administering to the subject an effective amount of a compound according to Formula (I), or a pharmaceutically acceptable salt thereof as a suitable pharmaceutically acceptable composition.

In another embodiment the present invention provides a method of treating liver failure in a subject, comprising administering to the subject an effective amount of a compound according to Formula (I), or a pharmaceutically acceptable salt thereof. The above and other embodiments of the present invention are disclosed further hereinafter.

DETAILED DESCRIPTION OF THE INVENTION

Figure 1:
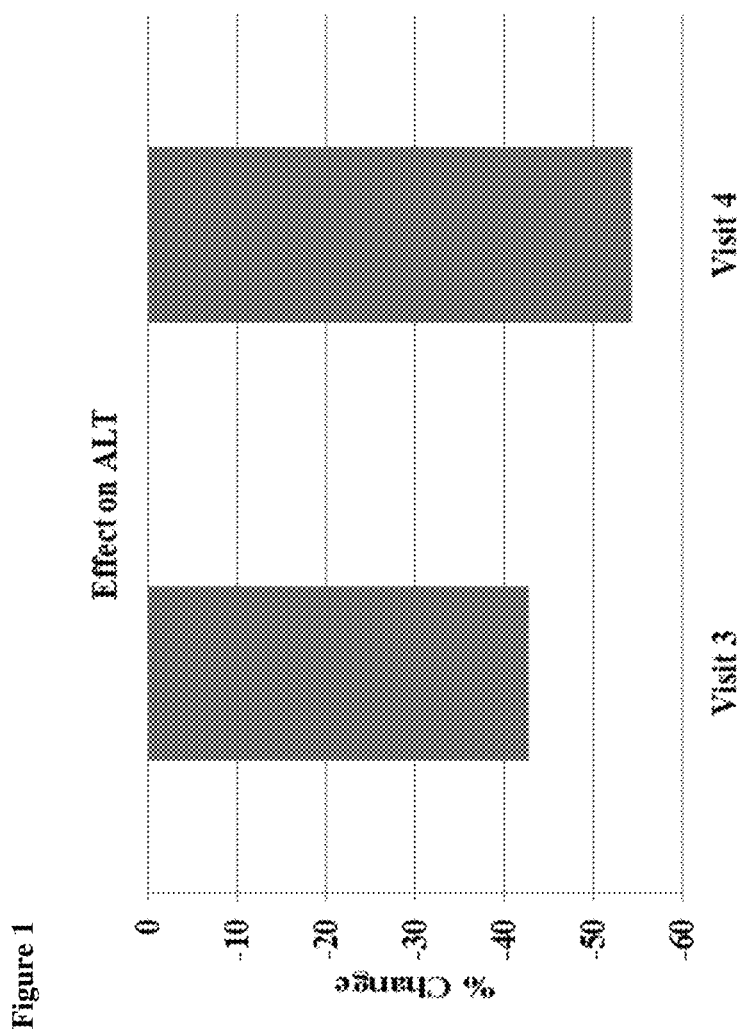
FIG. 1: Effect of magnesium salt of compound of formula (I) wherein R is -SMe on ALT in PP population.

The present invention describes a pharmaceutical composition for reduction and removal of lipid accumulated in the liver cells (hepatocytes), required for treating and preventing certain diseases and conditions in subject suffering from nonalcoholic fatty liver disease (NAFLD) including fatty liver (steatosis), nonalcoholic steatohepatitis (NASH), and cirrhosis (advanced scarring of the liver) and methods for ameliorating and/or treating such disease conditions.

The formulation comprises compound of formula (I) and the method comprises administering to a subject in need thereof an effective amount of a compound according to Formula (I), or a pharmaceutically acceptable salt thereof.

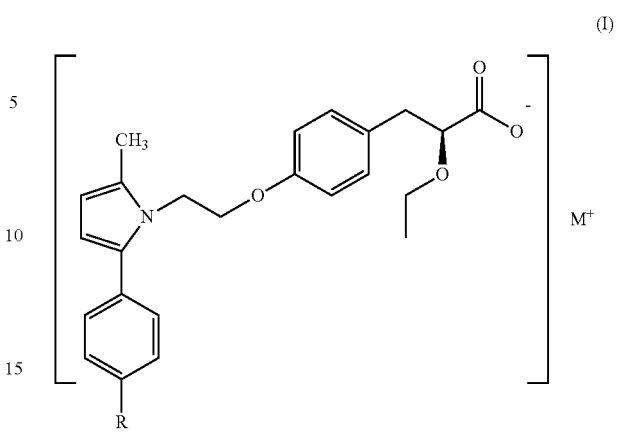

wherein 'R' is selected from hydroxy, hydroxyalkyl, acyl, alkoxy, alkylthio, thioalkyl, aryloxy, arylthio and $M^+$ represents suitable metal cations such as $Na^+$, $K^+$, $Ca^{+2}$, $Mg^{+2}$ and the like.

Definitions and Abbreviations

As used above, and throughout this disclosure, the following terms, unless otherwise indicated, shall be understood to have the following Meanings:

"Patient" includes both human and animals. "Mammal" means humans and other mammalian animals.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

As used herein "treating" includes achieving, partially or substantially, one or more of the following results: partially or totally reducing the extent of the disease, disorder or syndrome (e.g., reducing fat deposits, increasing insulin activity/sensitivity, reducing weight); ameliorating or improving a clinical symptom or indicator associated with the disorder; delaying, inhibiting or preventing the progression of the disease, disorder or syndrome; or partially or totally delaying, inhibiting or preventing the onset or development of disorder. Delaying, inhibiting or preventing the progression of the disease, disorder or syndrome includes for example, delaying, inhibiting or preventing the progression of fatty liver to NASH; delaying, inhibiting or preventing the progression of NASH to cirrhosis, end-stage liver disease and/or hepatocellular carcinoma; and delaying, inhibiting or preventing the progression of pre-diabetes to diabetes.

The term "alkyl" used herein, either alone or in combination with other radicals, denotes a linear or branched radical containing one to twelve carbons, such as methyl, ethyl, n-propyl, iso-propyl, n-butyl, sec-butyl, tert-butyl, amyl, t-amyl, n-pentyl, n-hexyl, iso-hexyl, heptyl, octyl and the like.

The term "alkoxy" used herein, either alone or in combination with other radicals, denotes a radical alkyl, as defined above, attached directly to an oxygen atom, such as methoxy, ethoxy, n-propoxy, iso-propoxy, n-butoxy, t-butoxy, iso-butoxy, pentyloxy, hexyloxy, and the like.

The term "aryl" or "aromatic" used herein, either alone or in combination with other radicals, refers to an optionally substituted aromatic system containing one, two or three rings wherein such rings may be attached together in a pendant manner or may be fused, such as phenyl, naphthyl, tetrahydronaphthyl, indane, biphenyl, and the like. The term "aralkyl" denotes an alkyl group, as defined above, attached to an aryl, such as benzyl, phenethyl, naphthylmethyl, and the like. The term "aryloxy" denotes an aryl radical, as defined above, attached to an alkoxy group, such as phenoxy, naphthyloxy and the like, which may be substituted. The term "aralkoxy" denotes an arylalkyl moiety, as defined above, such as benzyloxy, phenethyloxy, naphthylmethyloxy, phenylpropyloxy, and the like, which may be substituted.

The term "acyl" used herein, either alone or in combination with other radicals, refers to a radical containing one to eight carbons such as formyl, acetyl, propanoyl, butanoyl, iso-butanoyl, pentanoyl, hexanoyl, heptanoyl, benzoyl and the like, which may be substituted.

The term "hydroxyalkyl" used herein, either alone or in combination with other radicals, refers to an alkyl group, as defined above, substituted with one or more hydroxy radicals, such as hydroxymethyl, hydroxyethyl, hydroxypropyl, hydroxybutyl, hydroxypentyl, hydroxyhexyl and the like.

The term "thio($C_1$-$C_{12}$)alkyl" or "thio(($C_1$-$C_6$)alkyl" used herein, either alone or in combination with other radicals, represents an alkyl group, as defined above, attached to a group of formula —SR', where R' represents hydrogen, alkyl or aryl group, e.g. thiomethyl, methylthiomethyl, phenylthiomethyl and the like, which may be substituted "Effective amount" or "therapeutically effective amount" is meant to describe an amount of compound or a composition of the present invention effective in inhibiting the above-noted diseases and thus producing the desired therapeutic, ameliorative, inhibitory or preventative effect.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution- phase and isolatable solvates.

One or more compounds of the invention may optionally be converted to a solvate. Preparation of solvates is generally known. Thus, for example, M. Caira et al, J. Pharmaceutical Sci, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, AAPS Pharm Sci Tech., 5(1), article 12 (2004); and A. L. Bingham et al, Chem. Commun., 603-604 (2001)

The compounds of Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contain both a basic moiety, such as, but not limited to a pyridine or imidazole, and an acidic moiety, such as, but not limited to a carboxylic acid, zwitterions ("inner salts") may be formed and are also included within the term "salt(s)" as used herein.

Pharmaceutically acceptable (i.e., non-toxic, physiologically acceptable) salts are preferred, although other salts are also useful. Salts of the compounds of the Formula (I) may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonat.es (also known as tosylates,) and the like.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention Polymorphic forms of the compounds of Formula (I), and of the salts, solvates, esters and prodrugs of the compounds of Formula (I) are intended to be included in the present invention.

As used herein, the term "composition" is intended to encompass a product comprising the specified ingredients in the specified amounts, as well as any product which results, directly or indirectly, from combination of the specified ingredients in the specified amounts In the embodiments the present invention provides a suitable pharmaceutical composition of compounds of formula (I) or their derivatives, which comprises one or more pharmaceutical excipients, antioxidants and chelating agents, wherein the pH of the composition is above 6, preferably in the range from about pH 6 to pH of about 10.

In such embodiments the pharmaceutical composition of the present invention essentially comprises of
    the pharmaceutically active substance;
    Suitable additives;
    a suitable stabilizer;
    optionally with one or more pharmaceutically acceptable excipients.

One function of the liver is to process fats and proteins from digested food.

Fatty liver disease covers a range of conditions where there is a build-up of fat in the liver cells. The liver cells (hepatocytes) normally contain some fat and related fatty chemicals (triglycerides, fatty acids, etc). Excess fat is normally passed out of liver cells, into the bloodstream, and then taken up and stored in fat cells (adipose cells) throughout the body. In fatty liver disease, excess fat builds up in liver cells. This is thought to happen if there is some problem or disruption in the normal processing of fat and related fatty chemicals in the liver cells Simple fatty liver (also called "hepatic steatosis") is present when the fat content inside liver cells makes up more than 5-10% of the liver's weight. Simple fatty liver is not associated with serious damage or harm to the liver.

Nonalcoholic fatty liver disease (NAFLD) refers to a wide spectrum of liver disease ranging from: i) simple fatty liver (steatosis), in which there are fat deposits on the liver; ii) nonalcoholic steatohepatitis (NASH) in which there are fat deposits on the liver along with inflammation and damage of the liver; and iii) cirrhosis in which there is irreversible, advanced scarring of the liver.

All of the stages of NAFLD have in common the accumulation of fat (fatty infiltration) in the liver cells (hepatocytes). Fatty liver (steatosis) can progress to nonalcoholic steatohepatitis (NASH). In NASH, the fat accumulation is associated with varying degrees of inflammation and scarring of the liver, and in many cases insulin resistance, dyslipidemia and hypertension. NASH can progresses to fibrosing, steatohepatitis and may trigger cirrhosis, end-stage liver disease, acute live failure and hepatocellular carcinoma. It most often occurs in people with excess body weight, elevated blood lipids, such as cholesterol and triglycerides, and insulin resistance.

The present invention also provides methods of treating liver failure. Acute liver failure occurs when the cells in the liver die or become damaged in a short period of time. This causes the liver to fail to work normally and can be fatal.

Any progressive liver disease, such as cirrhosis, can result in liver failure. Signs of liver failure include encephalopathy (altered brain function, jaundice, ascites, fetor hepaticus and failure of coagulation).

Many people with simple fatty liver have other conditions where fatty liver is a complication. Many cases of simple fatty liver develop in people who drink more alcohol than the recommended limits Over half of people who drink heavily develop simple fatty liver. In these cases simple fatty liver can progress to alcoholic steatohepatitis. In this condition the excess fat in the liver cells is associated with, or may cause, inflammation of the liver. Alcoholic steatohepatitis, may eventually cause scarring (cirrhosis) of the liver.

Effective amounts of such compounds are administered to a subject with one or more of these conditions.

In an embodiments the compounds according to Formula (I) can be used alone or in combination e.g., as an adjunct therapy, with at least one other therapeutic agent. Compounds according to formula (I) can be subject with NASH, a compound according to formula (I) can be co-administered with a therapeutic agent used to reduce one or more of the symptoms of NASH or NAFLD including, but not limited to, an agent used to control blood glucose levels, an agent used to control lipid levels, e.g., an agent used to lower or control cholesterol, an antioxidant, an appetite suppressing agent, an anti-obesity agent, to control blood glucose levels, such as, sulfonylureas, an antibiotic/ probiotic or an anti-inflammatory agent. Examples of such agents are listed herein and includes chlorpropamide, glipizide, glyburide, and glimepiride; meglitinides, such as, repaglinide and nateglinide; biguanides, such as, metformin and acarbose; thiazolidinediones, such as, rosiglitazone, and pioglitazone; and insulin and its derivatives, such as, pramlintide, exenatide, humalog, novolog, humulin, novolin, ultralente, and lanrus; an agent used to control lipid levels, such as, vytorin, Clofibrate and Gemfibrozil, a plasma HDL-raising agent, a cholesterol lowering agent, a cholesterol biosynthesis inhibitor, for example an HMG-CoA reductase inhibitor (such as a statin, such as, Atorvastatin, Fluvastatin, Lovastatin, Pravastatin, Rosuvastatin, Simvastatin); an HMG-CoA synthase inhibitor, an acyl-coenzyme A: cholesterol acyl-transferase (ACAT) inhibitor, such as, melinamide; probucol, niacin (nicotinic acid, Vitamin-B-3), nicotinic acid and the salts thereof and niacinamide; a cholesterol absorption inhibitor such as ezetimibe; a bile acid sequestrant, such as, cholestyramine, colestipol, and Colesevelam; fibrates such as clofibrate, fenofibrate, and gemfibrizol, vitamin B6 (also known as pyridoxine) and physiologically acceptable salts thereof, such as the HCl salt; vitamin B12 (also known as cyanocobalamin), and angiotensin II antagonist converting enzyme inhibitor; a beta-blocker; an agent used to reduce weight or suppress appetite, such as, sibutramine, orlistat and the like.

In an embodiment, when methods of the present invention is used to treat a subject with alcoholic steatohepatitis, a compound according to formula (I) can be co-administered with a therapeutic agent used to reduce one or more of the symptoms of alcoholic steatohepatitis including, but not limited to, an agent used to control blood glucose levels, an agent used to control lipid levels, e.g., an agent used to lower control cholesterol, an antioxidant, an appetite suppressing agent, an anti-obesity agent, an antibiotic or an anti-inflammatory agent, such as those described above.

In another embodiments when used in the methods of the present invention to treat a subject with liver failure, a compound according to formula (I) can be co-administered with a therapeutic agent used to reduce one or more of the symptoms of alcoholic steatohepatitis including, but not limited to, an agent used to control blood glucose levels, an agent used to control lipid levels, such as those described above.

In a further embodiment, the present invention discloses a suitable pharmaceutical composition of the compound of formula (I), for the treatment of one or more of the diseases disclosed above. A preferred pharmaceutical composition of the compound of formula (I) comprises of
  the pharmaceutically active substance;
  Suitable additives;
  a suitable stabilizer;
  optionally with one or more pharmaceutically acceptable excipients.
Each of the components may be selected from those known in the art.

In an embodiment suitable stabilizers may be selected from the classes of antioxidants or chelating agents.

In an embodiment the pharmaceutical excepients according to the present invention can be selected from solubilizers, diluents, fillers, disintegrants, binder, lubricants, glidants, wetting agents, solvents and the like as is known in the art.

In an embodiment suitable additives are selected from sodium benzoate, sodium hydroxide, sodium sulfite and sodium carbonate.

In an embodiment antioxidants used according to the present invention include, but are not limited to citric acid, alpha tocopherol, sodium sulphite, sodium metabisulphite, butylated hydroxy anisole (BHA), BHT (2,6-di-tert-butyl-4-methylphenol), monothioglycerol, Vitamin C (ascorbic acid), and propyl gallate and combinations thereof and other similar material known to those of ordinary skilled in the art.

Chelating agent used according to the present invention include, but are not limited to Disodium EDTA, citric acid and or its salts, maleic acid, chlorambutol, chlorhexidine or its salts, chlorocresol, combinations thereof and other similar material known to those of ordinary skill in the art.

As used herein, the term "binders" is intended to mean substances used to cause adhesion of powder particles in tablet granulations. Such compounds include, by way of example and without limitation, acacia alginic acid, tragacanth, carboxymethylcellulose sodium, poly (vinylpyrrolidone), compressible sugar (e.g., NuTab), ethylcellulose, gelatin, liquid glucose, methyl cellulose, povidone and pregelatinized starch, combinations thereof and other similar material known to those of ordinary skill in the art.

When needed, other binders may also be included in the present invention. Exemplary binders include starch, poly (ethylene glycol), guar gum, polysaccharide, bentonites, sugars, invert sugars, poloxamers (PLURONIC F68, PLURONIC F127), collagen, albumin, celluloses in non-aqueous solvents, and the like or their suitable combinations. Other binders which may be included may be, for example, poly(propylene glycol), polyoxyethylene-polypropylene copolymer, polyethylene ester, polyethylene sorbitan ester, poly(ethylene oxide), microcrystalline cellulose, poly(vinylpyrrolidone), combinations thereof and other such materials known to those of ordinary skill in the art. As used herein, the term "diluent" or "filler" is intended to mean inert substances used as fillers to create the desired bulk, flow properties, and compression characteristics in the preparation of tablets and capsules. Such compounds include, by way of example and without limitation, dibasic calcium phosphate, kaolin, sucrose, mannitol, microcrystalline cellulose, powdered cellulose, precipitated calcium carbonate, sorbitol, starch, combinations thereof and other such materials known to those of ordinary skill in the art.

As used herein, the term "glidant" is intended to mean agents used in tablet and capsule formulations to improve flow-properties during tablet compression and to produce an anti-caking effect. Such compounds include, by way of example and without limitation, colloidal silica, calcium silicate, magnesium silicate, silicon hydrogel, cornstarch, talc, combinations thereof and other such materials known to those of ordinary skill in the art.

In an embodiment, the term "lubricant" is intended to mean substances used in tablet formulations to reduce friction during tablet compression. Such compounds include, by way of example and without limitation, calcium stearate, magnesium stearate, mineral oil, stearic acid, zinc stearate, suitable combinations thereof and other such materials known to those of ordinary skill in the art.

In an embodiment, the term "disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starched thereof, sweeteners, clays, such as bentonite, microcrystalline cellulose (e.g. Avicel™.), carsium (e.g. Amberlite.™.), alginates, sodium starch glycolate, gums such as agar, guar, locust bean, karaya, pectin, tragacanth, combinations thereof and other such materials known to those of ordinary skill in the art.

In an embodiment, the term "wetting agent" is intended to mean a compound used to aid in attaining intimate contact between solid particles and liquids. Exemplary wetting agents include, by way of example and without limitation, poloxamers, gelatin, casein, Glycerol mono-oleate, lecithin (phosphatides), gum acacia, cholesterol, tragacanth, stearic acid, benzalkonium chloride, calcium stearate, glycerol monostearate, cetostearyl alcohol,sodium lauryl sulphate, sodium dodecyl sulfate, salts of bile acids (taurocholate, glycocholate, cholate, deoxycholate, etc.), cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters, (e.g., TWEEN), polyethylene glycols, polyoxyethylene stearates colloidal silicon dioxide, phosphates, sodium dodecylsulfate, carboxymethylcellulose calcium, carboxy methylcellulosesodium,methyl cellulose,hydroxyethylcellulose, hydroxylpropylcellulose, hydroxy propyl methyl cellulose phthalate, noncrystalline cellulose, magnesium aluminum silicate, triethanolamine, polyvinyl alcohol, and poly vinyl pyrrolidone (PVP) and their suitable combinations and other such materials known to those of ordinary skill in the art. Tyloxapol (a nonionic liquid polymer of the alkyl aryl polyether alcohol type, also known as superinone or triton) is another useful wetting agent which may be used. The stable pharmaceutical composition according to the present invention may be in the form of tablet or capsule or a powder or a suspension in a liquid or an aerosol formulation or solutions, preferably in the form of tablet or capsule.

In another embodiment of the present invention, is a described process for the preparation of a stable pharmaceutical composition of compounds of formula (I) or their derivatives.

The stable pharmaceutical composition may be made by direct compression, wet granulation or dry granulation methods by techniques known to persons skilled in the art. Thus, for example, In wet granulation process, the drug is mixed with one or more pharmaceutical excepients and granulated with suitable binding solution as described earlier, to form wet granules, the wet granules are dried and optionally sieved. The dried granules are mixed with one or more suitable excipients from those described elsewhere and then compressed into tablets or filled into capsules.

In direct compression process, the drug is mixed with all the pharmaceutical excipients required and then is either compressed into tablets or filled in capsules.

In dry granulation process the drug is mixed with one or more pharmaceutical excipients and compressed into slugs and these slugs are passed through required sieve. The sieved granules are mixed with one or more suitable excipients from those described elsewhere and then compressed into tablets or filled into capsules.

One or more solvents used in the formulation are selected from acetone, chloroform, dichloromethane, ethyl alcohol, ethyl acetate, methyl alcohol, isopropyl alcohol and combinations thereof and other such materials known to those of ordinary skill in the art.

In an embodiment, the compound of formula (I) or pharmaceutical compositions containing the compound of formula (I) is given to a subject in need thereof at a dose of about 0.5 mg to 5 g. A skilled person is aware how to decide the optimum dose based on the patient profile, the severity of disease, the presence of secondary medicines and the like.

The compound of formula (I), when R is -SMe and $M^+$ is Mg, is dosed to patients in need thereof for the treatment of one or more of the diseases described above as per the following general protocol:

Study Design and Protocol:

Title of the Study—"A prospective, multi-centric, open-label, single arm study to evaluate the safety and efficacy of 4 mg of magnesium salt of compound of formula (I) wherein R is -SMe in a pharmaceutical composition as described above in Non-alcoholic steatohepatitis."

Objectives:

To evaluate the safety and efficacy of 4 mg of magnesium salt of compound of formula (I) wherein R is -SMe in Non-alcoholic steatohepatitis (NASH).

The following effficacy parameters were measured:
Primary Efficacy (Time Frame 6 and 12 Weeks):
 1. Change in alanine aminotransferase (ALT) from baseline Secondary Efficacy (Time Frame 6 and 12 Weeks):
 Sustained reduction in ALT level.
 C-peptide test for homeostasis model assessment (HOMA) beta and HOMA IR
 Triglyceride (TG)

Criteria for Safety:
 1. General and Systemic Clinical Examination: Cardiovascular system (CVS), respiratory system (RS), gastro-intestinal system (GIS), central nervous system (CNS) etc.
 2. Laboratory Investigations: Complete blood count (CBC), aspartate aminotransferase(AST), ALT, alkaline phosphatase (ALP), serum bilirubin, γ-glutamyl transpeptidase (GGT), Serum proteins, blood urea nitrogen (BUN), Serum creatinine, creatinine phosphokinase (CPK), fasting plasma glucose (FPG).
 3. Frequency and severity of adverse events (AEs) for all subjects enrolled were recorded. All AEs, were classified using
   causality
   severity
   seriousness Methodology:
It is an interventional, single arm, safety and efficacy study to explore effect of magnesium salt of compound of formula (I) wherein R is -SMe suitably formulated as described above, on NASH.

Subjects was diagnosed by biopsy as suffering from NASH in last one year and willing to participate in study were invited for screening programme for inclusion in the study.

Subjects satisfying inclusion exclusion criteria will be enrolled in the study.

All subjects were given suitable formulation of magnesium salt of compound of formula (I) wherein R is -SMe 4 mg for 12 weeks. Lifestyle modification was continued as before the study. Patient was monitored for safety and efficacy of magnesium salt of compound of formula (I) wherein R is -SMe.

Study Schedules:
Informed consent was obtained before any trial related activity.

Visit 1, Screening Visit/Enrollment [Week-1 to 0]
Subjects were screened for the inclusion and exclusion criteria and those qualifying were invited to participate in the study. Clinical evaluation was done for baseline characteristics and anthropometry After Clinical evaluations, all baseline safety and efficacy parameters were recorded as per Table (I) given below. All laboratory investigations were carried out after overnight fasting.

During the 12 week program, a designated person from the centre could interview the subjects for his/her general health, telephonically.

Enrolled Subjects would receive the study medication for next two weeks.

Patients were advised to follow same lifestyle modifications during study period as before the study.

Visit 2, [Week 2]
Subjects were clinically examined and given the study medications for four weeks and also safety parameters were assessed as per Table (I)given below.

Visit 3 [Week 6]
Subjects were clinically examined and given the study medications for next 6 weeks.
Safety and efficacy parameters were assessed as per Table (I) given below.

Visit 4 [Week 12]
Subjects were clinically examined and safety and efficacy parameters were assessed as per Table (I) given below.

If further investigations are required in case of any AE, investigator will be advised to assess the AE and take necessary action, if required. Subjects will be advised to contact the investigator for any complaints within next two weeks.

During the above period, if any subject misses the drug administration up to 3 consecutive days, it will not be considered drop-out or protocol deviation.

| Visit and Investigation Schedule | | | | |
|---|---|---|---|---|
| Activity | Screening/Enrolment Visit 1 (Week 0) | Visit2 (Week 2) | Visit 3 (Week 6) | Visit 4 (Week12/) |
| Demographics | | | | |
| Informed Consent | | | | |
| Inclusion/Exclusion criteria | | | | |
| Medical History | | | | |
| Clinical Examination | | | | |
| Laboratory studies (efficacy-Lipid profile, C peptide, ALT) | | | | |
| Laboratory studies* | | | | |
| ECG | | | | |
| USG | | | | |
| Pregnancy test for female subjects (advise for contraception) | | | | |
| Dispensing of Study Medication | | | | |
| Study Medication capsule Count | | | | |
| Recording of Adverse Events | | | | |
| Global Tolerability Assessments | | | | |
| Study Completion | | | | |

*Laboratory Tests:
Biochemistry (laboratory) parameters to be performed include following tests:
Liver Function test (LFT): AST, ALT, ALP, total bilirubin, serum proteins, total albumin and globulin, GGT
Renal function test: Blood urea nitrogen (BUN), Serum creatinine and calculated GFR
Creatinine phosphokinase (CPK)
CBC Criteria for Inclusion/Exclusion:
Inclusion Criteria
 Subject has given informed consent for participation in this trial
 Biopsy proven NASH (Biopsy done in last one year).
 ALT>than 1.5 times upper normal limit
 Patient presently on lifestyle modification for NASH for at least one month.
 BMI between 23 to 40 kg/m$^2$
 Compensated liver disease with the following hematologic, biochemical, and serological criteria on entry into protocol:
  Hemoglobin>9 gm/dL
  White blood cell (WBC)>2.5 K/UL
  Neutrophil count>1.5 K/UL
  Platelets>100 K/UL
  Serum bilirubin, <1.5mg%
  Albumin>3.2 g/dL Serum creatinine within normal limits Exclusion Criteria Pregnancy and lactation Subjects with history of gall stone Subjects with history of myopathies or evidence of active muscle diseases Subject with history of alcohol consumption>than 20 gm/week and/or drug abuse Known allergy, sensitivity or intolerance to the study drugs and their formulation ingredients.

Participation in any other clinical trial in past 3 months

History of malignancy; active neoplasm.

Previous liver biopsy that demonstrated presence of cirrhosis or radiologic imaging consistent with cirrhosis or portal hypertension Type 2 diabetes treated with agents other than the secretagogues (these include, insulin thiazolidinediones, alpha-glucosidase inhibitors, exenatide, pramlintide). Metformin will be allowed provided dose is stable science last 6 months.

Evidence of poorly-controlled diabetes [glycosylated hemoglobin (HbA1c)>9%].

Type I diabetes mellitus.

Abnormal PT/INR (Prothrombin Time/International normalized ratio)

Patient on fibrates (Other antidyslipidemic drugs will be allowed provided dose is stable in last 6 months)

Use of drugs associated with a clinical or histological picture consistent with fatty liver disease or NASH for more than 12 consecutive weeks in the 1 year prior to start of the study; (these include amiodarone, tamoxifen, methotrexate, glucocorticoids, anabolic steroids, tetracyclines, estrogens, valproate/valproic acid, chloroquine, anti-HIV drugs etc.)

History of thyroid disease poorly controlled on prescribed medications

History of, or current cardiac dysrhythmias and/or a history of cardiovascular disease, including myocardial infarction, except patients with only well controlled hypertension.

History of bariatric surgery, or undergoing evaluation for bariatric surgery.

History or other evidence of severe illness or any other conditions that would make the patient, in the opinion of the investigator, unsuitable for the study (such as poorly controlled psychiatric disease, coronary artery disease, or active gastrointestinal conditions that might interfere with drug absorption)

Subject on any treatment with other drugs claimed for treatment of NASH (Pentoxyphyllin, Ursodeoxycholic acid, acetyl cholinesterase enzyme (ACE) inhibitors antioxidants such as vitamin E, vitamin C, glutathione, alpha-tocopherol, or non-prescribed complementary alternative medications (including dietary supplements, megadose vitamins, herbal preparations, and special teas).) or any medicine in clinical trials for NASH.

Other cause of chronic liver disease [autoimmune, primary biliary cirrhosis, hepatitis B virus (HBV), Wilson, alpha-1-antitrypsin deficit, hemochromatosis etc.] i.e. Antinuclear antibodies (ANA)>1:160, Anti-smooth muscle Ab positive >1:160, Serum hepatitis B surface antigen (HepBsAg) positive, Serum hepatitis C antibody (HepC Ab) positive, transferrin saturation>45%

Results

Subjects were screened for inclusion in the study after obtaining informed consent, out of which 32 subjects were enrolled into the study. Out of these 32 subjects, 29 subjects completed the study.

The effect of magnesium salt of compound of formula (I) wherein R is -SMe at week 12 on various parameters of liver function is as below.

There was statistically significant reduction in the ALT levels from baseline in magnesium salt of compound of formula (I) wherein R is -SMe 4 mg treatment group in the PP population at visit 3 and visit 4. (FIG. 1)

There was sustained reduction in ALT levels 63.16% and 78.95% of patients at visit 3 and visit 4 respectively as per PP.

Figure 2:
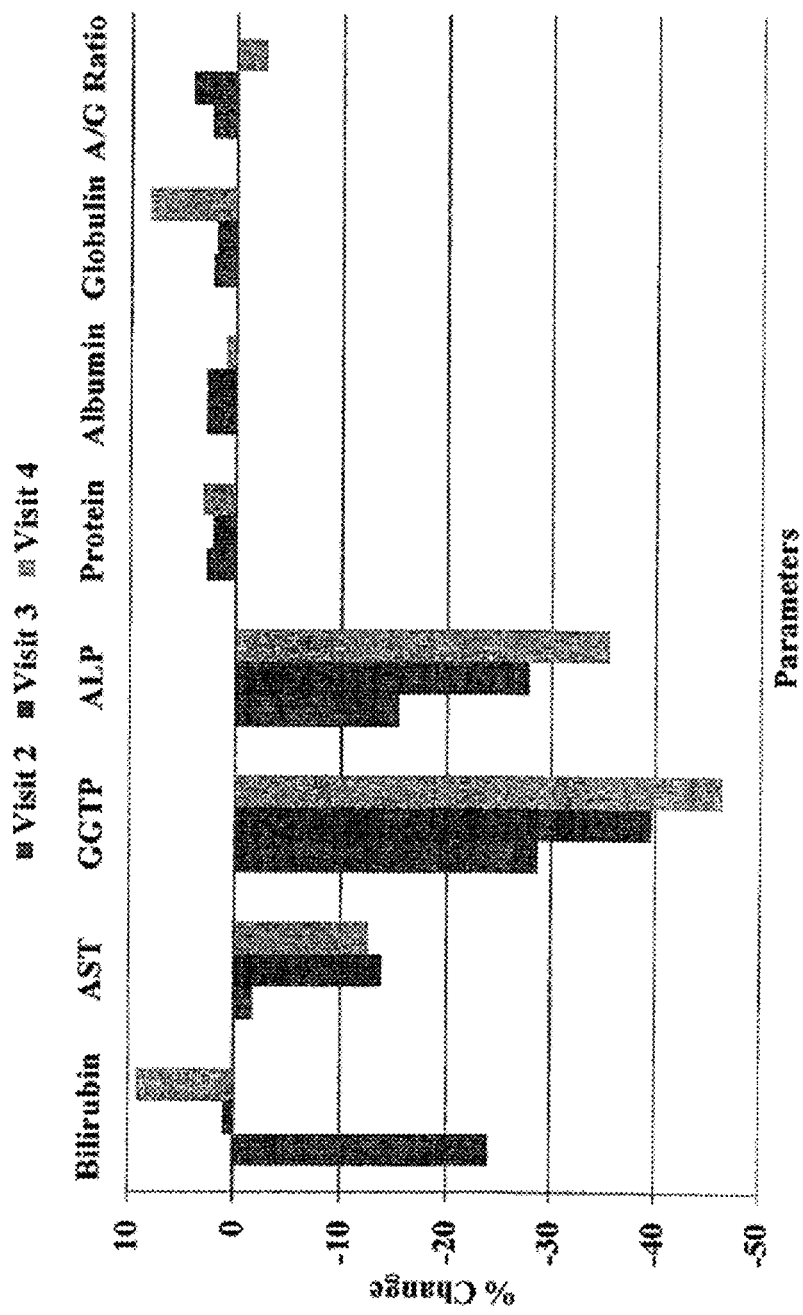
FIG. 2: Effect of magnesium salt of compound of formula (I) wherein R is -SMe on liver function test in Safety Population.

Magnesium salt of compound of formula (I) wherein R is -SMe showed a statistical significant decrease in the Aspartate Transaminase, gamma-glutamyl transpeptidase and alkaline phosphatase at Week 3 and at Week 4 in the Safety Population. (FIG. 2)

Figure 3:
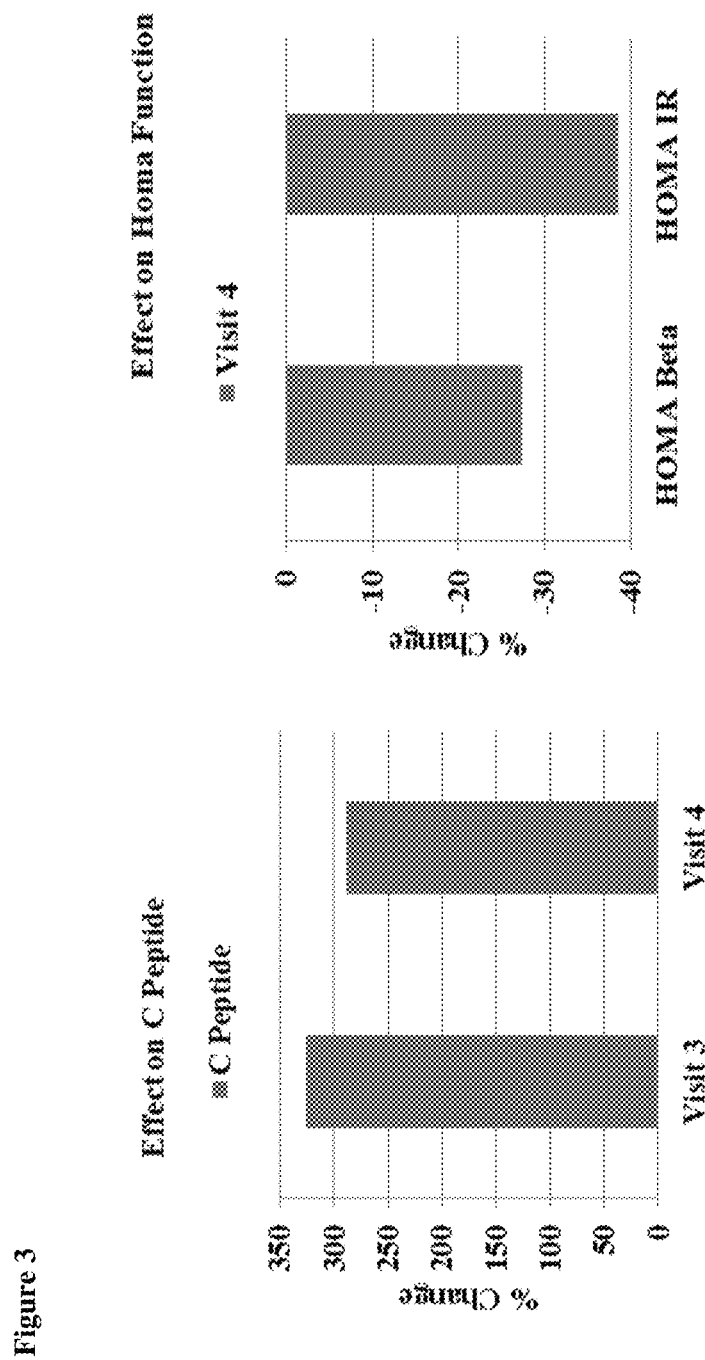
FIG. 3: Effect of magnesium salt of compound of formula (I) wherein R is -SMe on C-Peptide and HOMA Function in PP population.

There was a non-significant change in the C peptide levels in magnesium salt of compound of formula (I) wherein R is -SMe 4 mg at 6 and 12 weeks as per PP analysis and non-statistically significant reduction in HOMA—Beta cell function, HOMA—Insulin Resistance. (FIG. 3)

Figure 4:
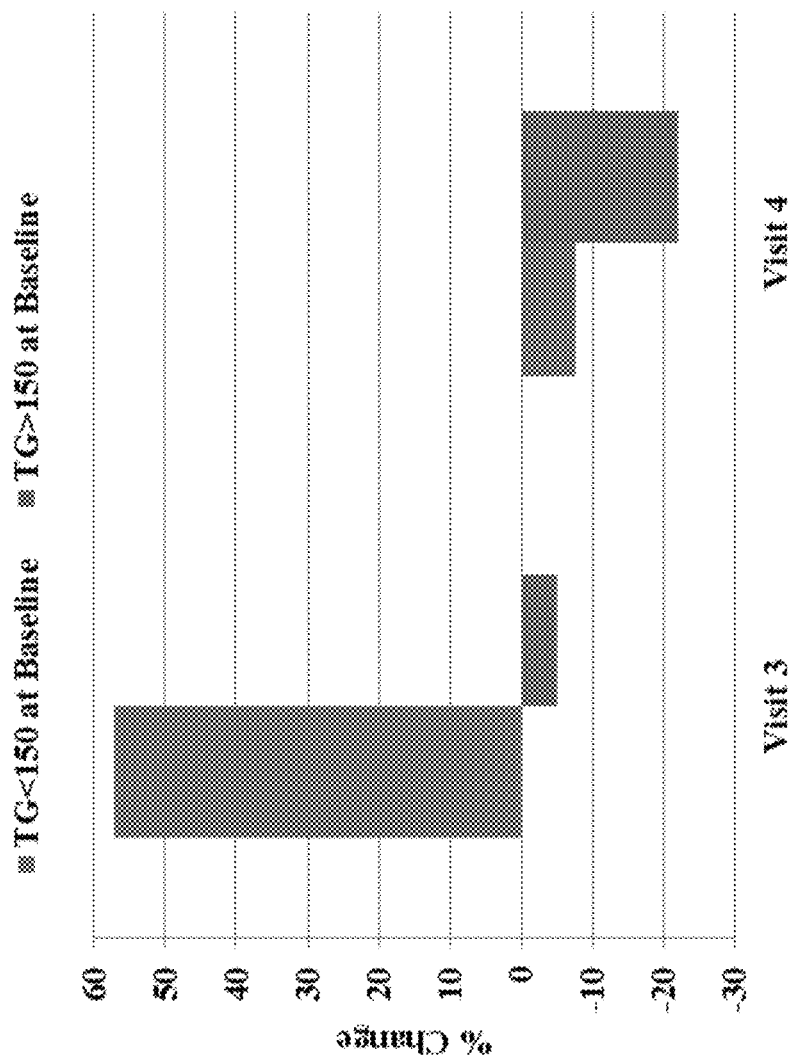
FIG. 4: Effect of magnesium salt of compound of formula (I) wherein R is -SMe on Triglycerides in PP population.

Baseline TG<150 mg/dl—There was decrease in triglyceride in magnesium salt of compound of formula (I) wherein R is -SMe 4 mg at week 12 as compared to baseline but it was not statistically significant in the PP population. (FIG. 4)

Baseline TG≥150 mg/dl—While decrease was observed in serum triglycerides at week 6 and 12 as compared to baseline but it was not statistically significant in magnesium salt of compound of formula (I) wherein R is -SMe 4 mg in PP population. (FIG. 4)

Safety Conclusion:

Overall, magnesium salt of compound of formula (I) wherein R is -SMe 4 mg was safe and well tolerated.

There were no deaths or SAEs reported in the magnesium salt of compound of formula (I) wherein R is -SMe 4 mg treatment arm.

The overall incidence of AEs was Nil.

There were no persistent changes from baseline in various laboratory parameters. Few events of raised creatinine and five events of raised CPK value were reported during the study. These events were mild and none of these events were considered clinically significant by the investigator.

There was no significant change in weight in magnesium salt of compound of formula (I) wherein R is -SMe 4 mg group in NASH patients at visit 2, 3 and 4 visits compared to baseline.

Thus, the compounds of the present invention and the pharmaceutical composition as described in the specification are suitable for reduction and removal of lipid accumulated in the liver cells (hepatocytes) for the treatment of Nonalcoholic fatty liver disease (NAFLD) which refers to a wide spectrum of liver diseases ranging from simple fatty liver (steatosis) to nonalcoholic steatohepatitis (NASH).

The invention claimed is:

1. A method of treating non-alcoholic steatohepatitis, comprising administering to a patient in need thereof a therapeutically effective amount of a pharmaceutical composition comprising a pharmaceutically acceptable salt of

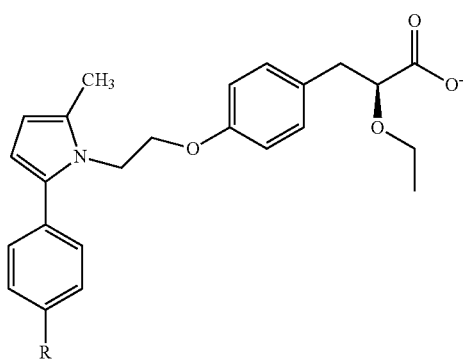

wherein R is —S-methyl, to treat the non-alcoholic steatohepatitis.

2. The method of claim 1, wherein the pharmaceutically acceptable salt is a metal cation salt.

3. The method of claim 1, wherein the pharmaceutically acceptable salt is a metal cation salt selected from the group consisting of a sodium salt, potassium salt, calcium salt, and magnesium salt.

4. The method of claim 1, wherein the pharmaceutically acceptable salt is a magnesium salt.

5. A method of treating non-alcoholic steatohepatitis, comprising administering to a patient in need thereof a therapeutically effective amount of a pharmaceutical composition comprising a pharmaceutically acceptable excipient and

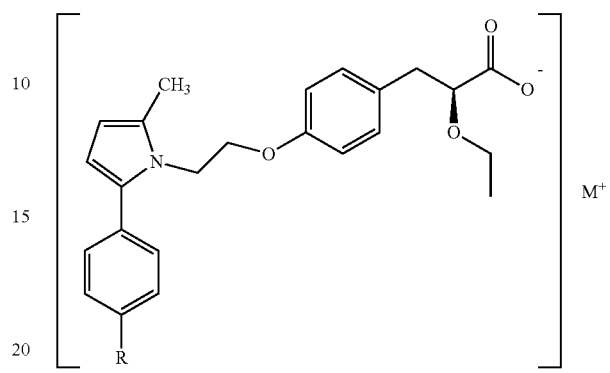

wherein R is —S-methyl, and $M^+$ is a metal cation, to treat the non-alcoholic steatohepatitis.

6. The method of claim 5, wherein $M^+$ is $Mg^{2+}$.

* * * * *